(12) United States Patent
Gagnon (10) Patent No.: US 6,211,523 B1
(45) Date of Patent: Apr. 3, 2001

(54) AUTOCONTOURING DEVICE FOR GAMMA CAMERA USING RADIOACTIVE SOURCE AND TRANSVERSE MOTION

(75) Inventor: Daniel Gagnon, Twinsburg, OH (US)

(73) Assignee: Picker International, Inc., Highland Heights, OH (US)

( * ) Notice: Subject to any disclaimer, the term of this patent is extended or adjusted under 35 U.S.C. 154(b) by 0 days.

(21) Appl. No.: 09/090,128

(22) Filed: Jun. 3, 1998

(51) Int. Cl.[7] ................................................. G01T 1/166
(52) U.S. Cl. .............................. 250/363.04; 250/363.02
(58) Field of Search ........................ 250/363.04, 363.02

(56) References Cited

U.S. PATENT DOCUMENTS

| | | |
|---|---|---|
| 4,158,776 | 6/1979 | Barrett . |
| 4,445,035 | 4/1984 | Ueyama . |
| 4,593,189 | 6/1986 | Stoub . |
| 5,072,121 | 12/1991 | Jazbee . |
| 5,319,205 | 6/1994 | Kline et al. . |
| 5,338,936 * | 8/1994 | Gullberg et al. ............ 250/363.04 |
| 5,376,796 | 12/1994 | Chan et al. . |
| 5,486,700 | 1/1996 | Silberklang et al. . |
| 5,600,145 | 2/1997 | Plummer . |
| 5,638,817 | 6/1997 | Morgan et al. . |
| 5,717,212 | 2/1998 | Fulton et al. . |
| 5,739,539 * | 4/1998 | Wang et al. ................. 250/363.04 |

FOREIGN PATENT DOCUMENTS

| | | |
|---|---|---|
| 747731A2 | 12/1996 | (EP) . |
| 2967918 | 5/1994 | (FR) . |
| WO 97/36189 | 10/1997 | (WO) . |

\* cited by examiner

*Primary Examiner*—Constantine Hannaher
*Assistant Examiner*—Andrew Israel
(74) *Attorney, Agent, or Firm*—Fay, Sharpe, Fagan, Minnich & McKee, LLP (57) ABSTRACT

A nuclear medicine gamma camera for diagnostic imaging includes a rotating gantry (16) which defines a subject receiving aperture (18). A support (10) supports a subject (12) being examined within the subject receiving aperture (18). A plurality of detector heads (20*a–c*) is movably attached to the rotating gantry (16). The detector heads (20*a–c*) are rotated about the subject (12) with the rotation of the rotating gantry (16). A plurality of radiation sources (30*a–c*) are mounted to the detector heads (20*a–c*) such that transmission radiation (32*a–c*) from the radiation sources (30*a–c*) is directed toward and received by corresponding detector heads (20*a–c*) positioned across the subject receiving aperture (18) from the radiation sources (30*a–c*). Translation means (22*a–c*) independently translates the detector heads (20*a–c*) laterally in directions tangential to the subject receiving aperture (18). A contouring device (40) runs a contouring operation wherein the translation means (22*a–c*) translates the detector heads (20*a–c*) laterally, and the contouring device (40) measures outer boundaries of the subject (12) in response to the transmission radiation (32*a–c*) received by the detector heads (20*a–c*).

19 Claims, 4 Drawing Sheets

AUTOCONTOURING DEVICE FOR GAMMA CAMERA USING RADIOACTIVE SOURCE AND TRANSVERSE MOTION

BACKGROUND OF THE INVENTION

The present invention relates to the arts of nuclear medicine and diagnostic imaging. It finds particular application in conjunction with gamma cameras, and will be described with particular reference thereto. It is to be appreciated that the present invention is amendable to single photon emission computed tomography (SPECT), whole body nuclear scans, positron emission tomography (PET), compton scattering, other diagnostic modes, and/or other like applications.

Diagnostic nuclear imaging is used to study a radionuclide distribution in a subject. Typically, one or more radiopharmaceuticals or radioisotopes are injected into a subject. The radiopharmaceuticals are commonly injected into the subject's blood stream for imaging the circulatory system or for imaging specific organs which absorb the injected radiopharmaceuticals. Gamma or scintillation camera detector heads, typically including a collimator, are placed adjacent to a surface of the subject to monitor and record emitted radiation. Often, the head is rotated or indexed around the subject to monitor the emitted radiation from a plurality of directions. The monitored radiation data from the multiplicity of directions is reconstructed into a three dimensional image representation of the radiopharmaceutical distribution within the subject.

One of the problems with this imaging technique is that photon absorption and scatter by portions of the subject between the emitting radionuclide and the camera head distort the resultant image. One solution for compensating for photon attenuation is to assume uniform photon attenuation throughout the subject. That is, the subject is assumed to be completely homogenous in terms of radiation attenuation with no distinction made for bone, soft tissue, lung, etc. This enables attenuation estimates to be made based on the surface contour of the subject. Of course, human subjects do not cause uniform radiation attenuation, especially in the chest.

In order to obtain more accurate radiation attenuation measurements, a direct measurement is made using transmission computed tomography techniques. In this technique, radiation is projected from a radiation source through the subject. Radiation that is not attenuated is received by detectors at the opposite side. The source and detectors are rotated to collect transmission data concurrently with the emission data through a multiplicity of angles. This transmission data is reconstructed into an image representation using conventional tomography algorithms. The radiation attenuation properties of the subject from the transmission computed tomography image are used to correct for radiation attenuation in the emission data.

Often, the detector heads of gamma cameras are movably mounted to a rotating gantry. Generally, they enjoy various degrees of freedom with respect to the rotating gantry, including: being movable radially toward and away from the subject; being circumferentially adjustable relative to the rotating gantry; and/or, being laterally translated in tangential directions to facilitate irising of the detector heads.

Generally, the resolution of the collimated detector deteriorates with increased distance from the face of the collimator. Thus, it is desirable to place the gamma camera as close as possible to the patient to reduce the blurring caused by the distance-dependent system response function and to minimize loss of resolution. To accomplish this, non-circular orbits are used in which the detectors closely follow the body contour. To prevent possible injury, a peanut or oval contour is desired so that the detector heads avoid contact with the subject while remaining as close as possible. Moreover, accurate subject contour information improves reconstruction.

Various proximity, boundary, and/or contour determining techniques have been developed to address these issues. Generally, these techniques employ additional costly and/or cumbersome hardware that is fitted to the gamma camera. In some instances, the hardware employed is light sources and detectors to sense a break in the transmission of the light from the source to the detector caused by an interruption from an edge of the subject. However, in addition to the extra hardware employed, these techniques may be unreliable due to interference from ambient sun light.

The present invention contemplates a new and improved autocontouring device which overcomes the above-referenced problems and others.

SUMMARY OF THE INVENTION

In accordance with one aspect of the present invention, a nuclear medicine gamma camera for diagnostic imaging includes a rotating gantry which defines a subject receiving aperture. A support supports a subject being examined within the subject receiving aperture. A plurality of detector heads are movably attached to the rotating gantry. The detector heads rotate about the subject with the rotation of the rotating gantry. A plurality of radiation sources are mounted to the detector heads such that transmission radiation from the radiation sources is directed toward and received by corresponding detector heads positioned across the subject receiving aperture from the radiation sources. Translation means independently translate the detector heads laterally in directions tangential to the subject receiving aperture. A contouring device runs a contouring operation wherein the translation means translates the detector heads laterally and the contouring device measures outer boundaries of the subject in response to the transmission radiation received by the detector heads.

In accordance with a more limited aspect of the present invention, while running the contouring operation, the rotating gantry is incrementally rotated such that the contouring device measures outer boundaries of the subject at a number of angular orientations to obtain a contour of the subject.

In accordance with a more limited aspect of the present invention, the contour of the subject is obtained prior to running an imaging operation.

In accordance with a more limited aspect of the present invention, the plurality of detector heads includes a first detector head and a second detector head arranged on the rotating gantry on opposite sides of the subject receiving aperture such that radiation receiving faces of the first and second detector heads face one another. The plurality of radiation sources includes a first radiation source mounted to the first detector head such that transmission radiation from the first radiation source is directed toward and received by the second detector head. The plurality of radiation sources also includes a second radiation source mounted to the second detector head such that transmission radiation from the second radiation source is directed toward and received by the first detector head.

In accordance with a more limited aspect of the present invention, the first and second radiation sources are mounted at opposite ends of the radiation receiving faces of the first and second detector heads, respectively.

In accordance with a more limited aspect of the present invention, while running the contouring operation, the translation means translates the first and second detector heads laterally in opposite directions.

In accordance with a more limited aspect of the present invention, the plurality of detector heads includes a first detector head, a second detector head, and a third detector head arranged on the rotating gantry spaced apart from one another about the subject receiving aperture. The plurality of radiation sources includes: a first radiation source mounted to the first detector head such that transmission radiation from the first radiation source is directed toward and received by the second detector head; a second radiation source mounted to the second detector head such that transmission radiation from the second radiation source is directed toward and received by the third detector head; and, a third radiation source mounted to the third detector head such that transmission radiation from the third radiation source is directed toward and received by the first detector head.

In accordance with a more limited aspect of the present invention, the individual detector heads are selectively movable in a radial direction relative to the subject receiving aperture.

In accordance with a more limited aspect of the present invention, while running the imaging operation, the detector heads are radially positioned such that an orbit traced by the detector heads as the rotating gantry rotates is determined in response to the contour of the subject obtained during the contouring operation.

In accordance with another aspect of the present invention, a method of mapping outer boundaries of a subject being examined with a nuclear medicine gamma camera is provided. It includes placing the subject in a subject receiving aperture. A plurality of radiation sources and corresponding radiation detectors are positioned about the subject receiving aperture such that the radiation sources are across the subject receiving aperture from their corresponding radiation detectors. Radiation from the radiation sources is directed toward corresponding radiation detectors positioned across the subject receiving aperture. The relative positions of the radiation sources with respect to their corresponding radiation detectors is changed, and the outer boundaries of the subject are measured in response to the radiation received by the radiation detectors.

In accordance with a more limited aspect of the present invention, the method further includes incrementally rotating the radiation sources and corresponding radiation detectors about the subject receiving aperture such that measurements of the outer boundaries of the subject are taken at a number of angular orientations. A contour of the subject is obtained from the measurements.

In accordance with a more limited aspect of the present invention, the step of changing the relative positions of the radiation sources with respect to their corresponding radiation detectors further includes translating the radiation sources laterally in directions tangential to the subject receiving aperture.

In accordance with a more limited aspect of the present invention, the step of changing the relative positions of the radiation sources with respect to their corresponding radiation detectors further includes concurrently with the translation of the radiation sources, translating the radiation detectors laterally and directions tangential to the subject receiving aperture.

In accordance with a more limited aspect of the present invention, the plurality of radiation sources includes two radiation sources and the step of changing the relative positions of the radiation sources with respect to their corresponding radiation detectors further includes translating the two radiation sources laterally in directions opposite one another and tangential to the subject receiving aperture.

In accordance with a more limited aspect of the present invention, the method further includes fixedly positioning each of the radiation sources on one of the radiation detectors and translating the radiation detectors laterally in directions tangential to the subject receiving aperture.

In accordance with a more limited aspect of the present invention, the method further includes an imaging operation wherein the radiation sources and corresponding radiation detectors are selectively moved in a radial direction relative to the subject receiving aperture in response to the obtained contour.

In accordance with a more limited aspect of the present invention, the method further includes rotating the radiation sources and corresponding radiation detectors about the subject receiving aperture such that their orbit is determined in response to the obtained contour of the subject.

One advantage of the present invention is that a subject's contour is accurately and efficiently measured.

Another advantage of the present invention is that safe placement of detector heads with a minimum orbit is achieved by having an accurate contour.

Another advantage of the present invention is improved image quality is achieved resulting from close positioning of the detector heads.

Another advantage of the present invention is that information obtained from measuring the subject's contour improves efficiency of tomographic reconstruction.

Another advantage of the present invention is that an improved image contouring system is achieved in a gamma camera without additional hardware.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
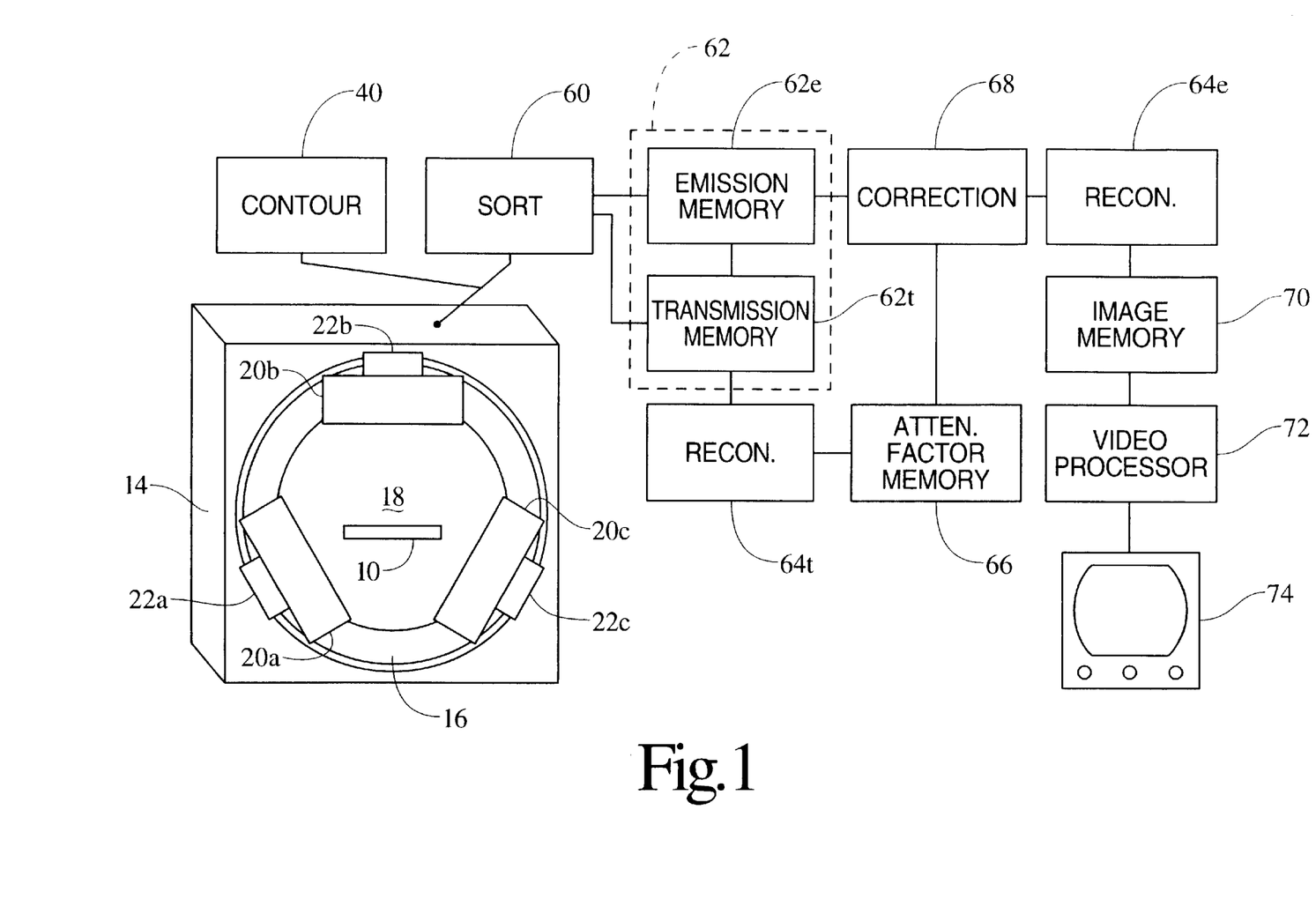
FIG. 1 is a diagrammatic illustration of a nuclear medicine gamma camera in accordance with aspects of the present invention.

With reference to FIG. 1, a diagnostic imaging apparatus includes a subject support 10, such as a table or couch, which supports a subject 12 (see FIGS. 2A and 2B) being examined and/or imaged. The subject 12 is injected with one or more radiopharmaceuticals or radioisotopes such that emission radiation is emitted therefrom. Optionally, the subject support 10 is selectively height adjustable so as to center the subject 12 at a desired height. A first gantry 14 holds a rotating gantry 16 rotatably mounted thereto. The rotating gantry 16 defines a subject receiving aperture 18. In a preferred embodiment, the first gantry 14 is advanced toward and/or retracted from the subject support 10 so as to selectively position regions of interest of the subject 12 within the subject receiving aperture 18. Alternately, the subject support 10 is advanced and/or retracted to achieve the desired positioning of the subject 12 within the subject receiving aperture 18.

Detector heads 20a–c are movably mounted to the rotating gantry 16. The detector heads 20a–20c also rotate about the subject receiving aperture 18 (and the subject 12 when located therein) with the rotation of the rotating gantry 16. Optionally, the detector heads 20a–c are circumferentially adjustable to vary their spacing on the rotating gantry 16 as for example in the manner disclosed in U.S. Pat. No. 5,717,212, incorporated herein by reference. Separate translation devices 22a–c, such as motors and drive assemblies, independently translate the detector heads laterally in directions tangential to the subject receiving aperture 18 along linear tracks or other appropriate guides. Additionally, the detector heads 20a–c are also independently movable in radial directions with respect to the subject receiving aperture 18. Alternately, a single motor and drive assembly controls movement of all the detector heads 20a–c individually and/or as a unit.

Each of the detector heads 20a–c has a radiation receiving face facing the subject receiving aperture 18 that includes a scintillation crystal, such as a large doped sodium iodide crystal, that emits a flash of light or photons in response to incident radiation. An array of photomultiplier tubes receive the light and convert it into electrical signals. A resolver circuit resolves the x,y-coordinates of each flash of light and the energy of the incident radiation. That is to say, radiation strikes the scintillation crystal causing the scintillation crystal to scintillate, i.e., emit light photons in response to the radiation. The photons are directed toward the photomultiplier tubes. Relative outputs of the photomultiplier tubes are processed and corrected to generate an output signal indicative of (1) a position coordinate on the detector head at which each radiation event is received, and (2) an energy of each event. The energy is used to differentiate between various types of radiation such as multiple emission radiation sources, stray and secondary emission radiation, transmission radiation, and to eliminate noise. An image representation is defined by the radiation data received at each coordinate. The radiation data is then reconstructed into an image representation of a region of interest.

Optionally, the detector heads 20a–c include mechanical collimators (not shown) removably mounted on the radiation receiving faces of the detector heads 20a–c. The collimators preferably include an array or grid of lead vanes which restrict the detector heads 20a–c from receiving radiation not traveling along selected rays in accordance with the data type being collected.

Figure 2A:
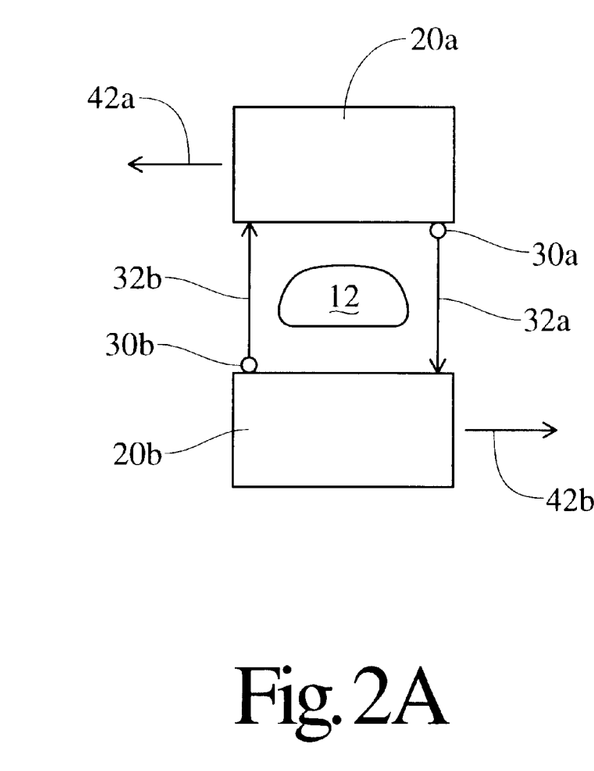
FIGS. 2A and 2B are diagrammatic illustrations showing the detector heads of two and three head embodiments, respectively, of the nuclear medicine gamma camera ir accordance with aspects of the present invention.
Figure 2B:
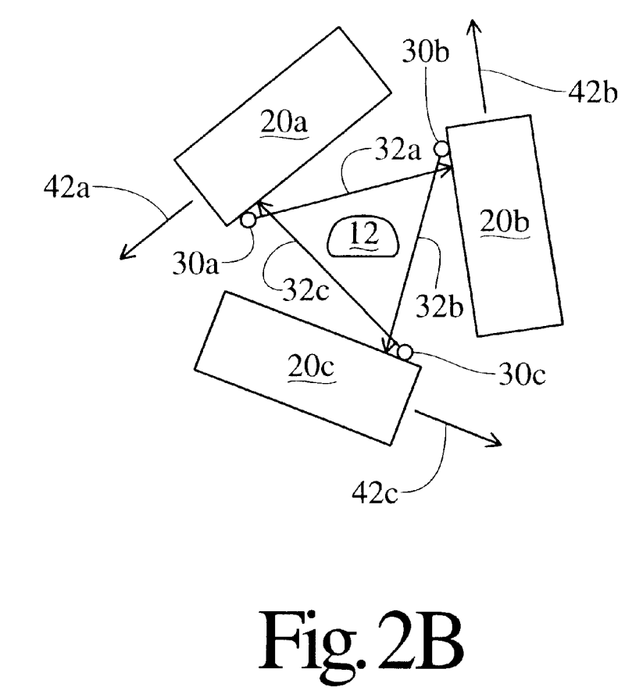

With reference to FIGS. 2A and 2B, and continuing reference to FIG. 1, radiation sources 30a–c are mounted to the radiation receiving faces of the detector heads 20a–c such that transmission radiation (represented by the arrows 32a–c) from the radiation sources 30a–c is directed toward and received by corresponding detector heads 20a–c positioned across the subject receiving aperture from the radiation sources 30a–c. In a preferred embodiment, collimators are employed on the detector heads 20a–c which, in effect, collimates the transmission radiation 32a–c. That is to say, the collimators restrict the detector heads 20a–c from receiving those portions of transmission radiation not traveling along rays normal to the radiation receiving faces of the detector heads 20a–c. Alternately, other collimation geometries are employed for different applications and/or the collimation may take place at the source.

FIG. 2A illustrates a two head embodiment including a first detector head 20a and a second detector head 20b arranged on the rotating gantry 16 on opposite sides of the subject receiving aperture 18 such that the radiation receiving faces of the first and second detector heads 20a,b face one another. A first radiation source 30a is mounted to the first detector head 20a such that transmission radiation 32a therefrom is directed toward and received by the second detector head 20b. A second radiation source 30b is mounted to the second detector head 20b such that transmission radiation 32b therefrom is directed toward and received by the first detector head 20a. The first and second radiation sources 30a,b are mounted at opposite ends of the radiation receiving faces of the first and second detector heads 20a,b, respectively.

FIG. 2B illustrates a three head embodiment including a first detector head 20a, a second detector head 20b, and a third detector head 20c arranged on the rotating gantry 16 spaced from one another around the subject receiving aperture 18. A first radiation source 30a is mounted to the first detector head 20a such that transmission radiation 32a therefrom is directed toward and received by the second detector head 20b. A second radiation source 30b is mounted to the second detector head 20b such that transmission radiation 32b therefrom is directed toward and received by the third detector head 20c. A third radiation source 30c is mounted to the third detector head 20c such that transmission radiation 32c therefrom is directed toward and received by the first detector head 20a. In the three10 head configuration, iris-like movement of the detector heads 20a–c is achieved through a combination of tangential and radial movement. In this manner, the detector heads 20a–c are advanced toward and retracted from the subject 12 without mechanically interfering with one another.

Optionally, the three head embodiment is employed as a two head system by circumferentially adjusting the position of two of the heads so that they are located on opposing sides of the subject receiving aperture 18. In this configuration, the third head may be employed to provide additional diagnostic information or may be moved back to its farthest radial position and turned off.

In any case, the radiation sources 30a–c are line sources each extending across a length of the respective detector heads 20a–c to which they are mounted. Preferably, the lines sources are thin steel tubes filled with radionuclides and sealed at their ends. Alternately, the radiation sources 30a–c are bar sources, point sources, flat rectangular sources, disk sources, flood sources, a tube or vessel filled with radionuclides, or active radiation generators such as x-ray tubes. Additionally, the radiation sources 30a–c may be slidably mounted to the face of the detector heads 20a–c as for example in the manner disclosed in U.S. Pat. Nos. 5,600,145 and 5,638,817, incorporated herein by reference.

Alternately, one or more point sources of transmission radiation may be utilized.

With reference to FIGS. 1, 2A, and 2B, prior to running an imaging operation, a contour device 40 runs a contouring operation to measure the outer contour of the subject 12. During the contouring operation, the translation means 22a–c translate the detector heads 20a–c laterally in directions (indicated by the arrows 42a–c) tangential to the subject receiving aperture 18, and the contouring device 40 measures outer boundaries of the subject 12 in response to the transmission radiation 32a–c received by the detector heads 20a–c. The edges of the subject 12 are registered when the subject 12 interferes with the transmission radiation 32a–c emitted from the radiation sources 30a–c as detected by the corresponding detector heads 20a–c (see FIGS. 3A and 3B). That is to say, as the relative positions of the radiation sources 30a–c and the corresponding detector heads 20a–c which receive the transmission radiation 32a–c therefrom are varied, eventually the outer boundary of the subject 12 interferes with and/or crosses the path of the transmission radiation 32a–c as it is transmitted across the subject receiving aperture 18. This is detected by the detector heads 20a–c, and the outer boundary of the subject 12 is measured relative to the positions of the radiation sources 30a–c and the detector heads 20a–c. Repeatedly, the rotating gantry 16 is incrementally rotated with the contouring device 40 measuring the outer boundaries of the subject 12 at a number of angular orientations to obtain a complete outer contour of the subject 12.

Figure 3A:
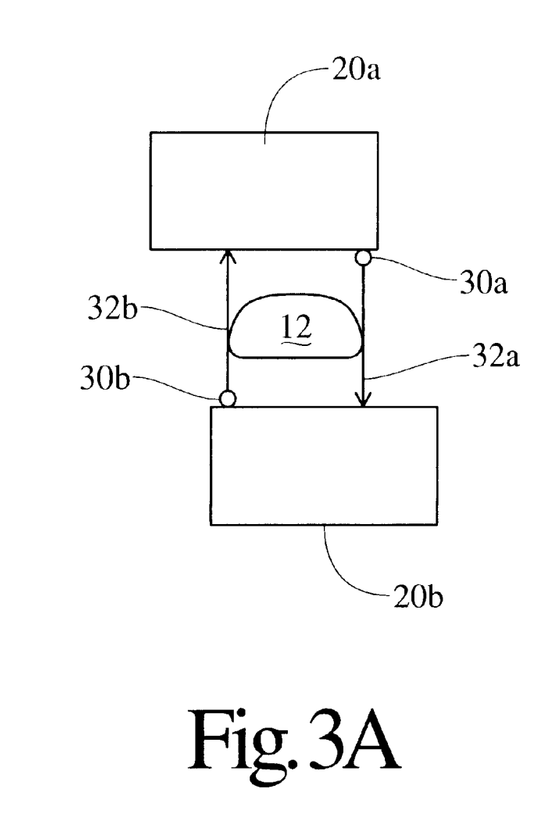
FIGS. 3A and 3B are diagrammatic illustrations corresponding to FIGS. 2A and 2B, respectively, wherein the detector heads have been translated to the point where the outer boundaries of the subject are interfering with the transmission radiation from the radiation sources such that the edges are registered in accordance with aspects of the present invention; and, FIGS. 4A and 4B are diagrammatic illustration of the detector heads fitted with dedicated sources and detectors for measuring the contour of the subject in accordance with aspect of the present invention.
Figure 3B:
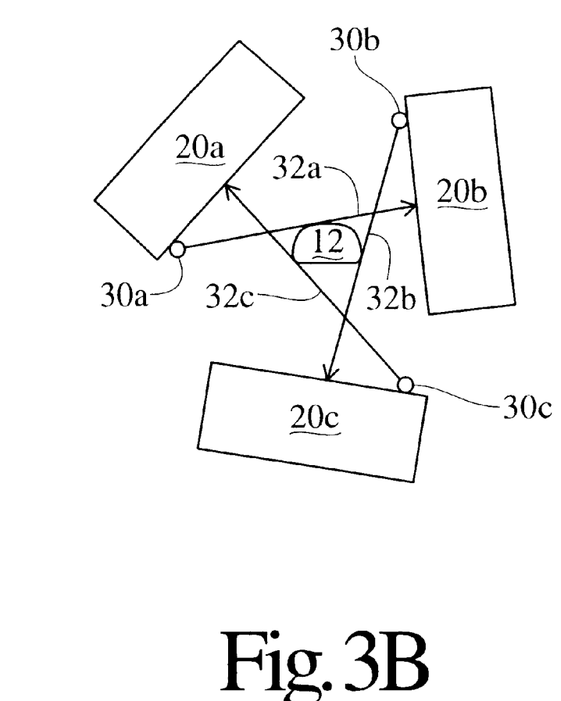

In a preferred two head embodiment as illustrated in FIGS. 2A and 3A, where the radiation sources 30a,b are mounted at opposite ends of the faces of the detector heads 20a,b, the detector heads 20a,b are laterally translated in opposite directions 42a,b during the contouring operation so that two outer boundaries points on opposite sides of the subject 12 are measured without changing the directions of the translations. With the three head configuration as illustrated in FIGS. 2B and 3B, three outer boundaries points of the subject 12 are measure for each translation of the detector heads 20a–c. In a preferred alternate embodiment, wherein the radiation sources 30a–c are slidably mounted to faces of the detector heads 20a–c, rather than laterally translating the detector heads 20a–c, the radiation sources 30a–c are themselves slid across the faces of the detector heads 20a–c to vary the relative positions of the radiation sources 30a–c to their respective detector heads 20a–c.

Figure 4A:
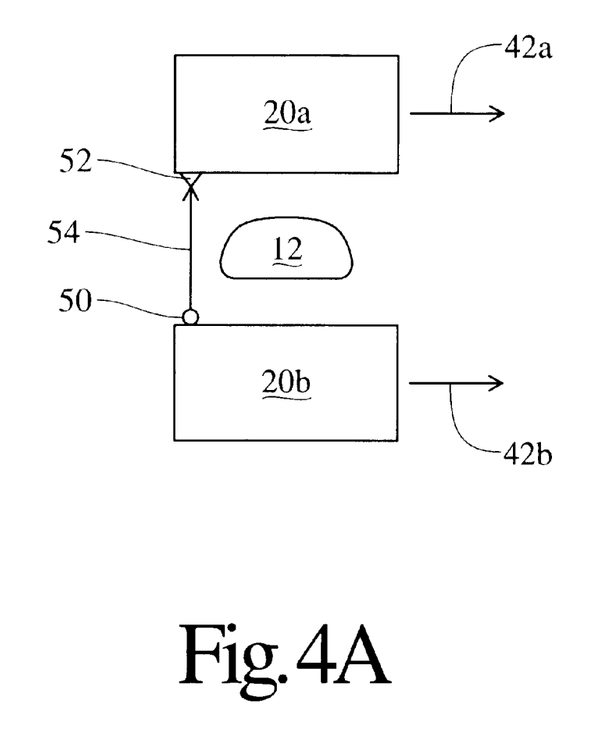
Figure 4B:
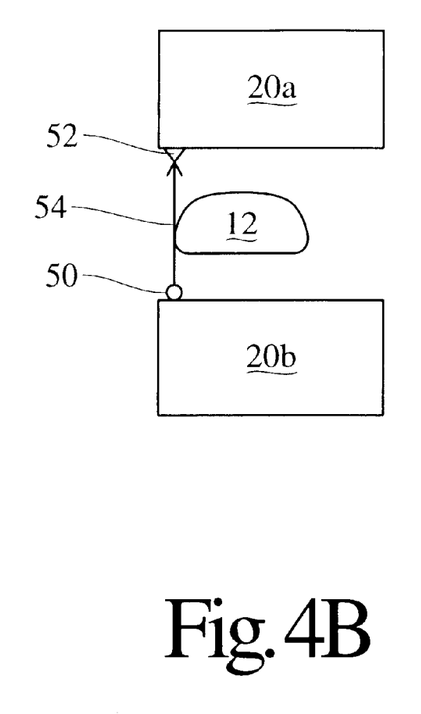

In an alternate embodiment illustrated in FIGS. 4A and 4B, the detector heads 20a,b are fitted with dedicated sources 50 and detectors 52 that employ alternate forms of radiation such as light or infrared radiation (represented by the arrow 54). Opposing detector heads 20a,b are fitted with corresponding dedicated sources 50 and detectors 52 such that as the detector heads 20a,b are translated in the contouring operation and the subject 12 interrupts (see FIG. 4B) the radiation 54 traveling from the source 50 to the detector 52 an edge is registered.

In any event, having obtained the outer contour of the subject 12, the detector heads 20a–c are safely positioned radially about the subject 12 such that contact with the subject 12 and potential injury to the subject 12 during the running of the imaging operation is avoided. Moreover, the detector heads 20a–c are radially or otherwise adjusted on the fly in response to the contour such that a minimum orbit or other desired orbit or trajectory relative to the contour of the subject 12 is traced by the detector heads 20a–c as the rotating gantry 16 rotates in the imaging operation. Additionally, the contour information is used in the tomographic reconstruction.

With reference again to FIG. 1, running an imaging operation includes a reconstruction technique for emission and transmission data. Of course, the reconstruction technique changes according to the types of radiation collected and the types of collimators used (i.e. fan, cone, parallel beam, and/or other modes). Emission radiation from the subject 12 and transmission radiation 32a–c from the radiation sources 30a–c is received by the detector heads 20a–c, and emission projection data and transmission projection data is generated. The emission data normally contains inaccuracies caused by varying absorption characteristics of the subject's 12 anatomy. A sorter 60 sorts the emission projection data and transmission projection data on the basis of their relative energies. The data is stored in a projection view memory 62, more specifically in corresponding emission data memory 62e and transmission data memory 62t. A reconstruction processor 64t reconstructs the transmission data into a transmission image representation or volume of attenuation factors stored in a memory 66. Each voxel value stored in the memory 66 is indicative of attenuation of tissue in a corresponding location within the subject 12. An emission data correction means 68 corrects the emission data in accordance with the attenuation factors determined from the transmission data. More specifically, for each ray along which emission data is received, the emission correction means 68 calculates a corresponding ray through the transmission attenuation factors stored in the memory 66. Each ray of the emission data is then weighted or corrected 68 in accordance with the attenuation factors and reconstructed by an emission radiation reconstruction processor 64e to generate a three-dimensional emission image representation that is stored in a volumetric image memory 70. A video processor 72 withdraws selected portions of the data from the image memory 70 to generate corresponding human-readable displays on a video monitor 74. Typical displays include reprojections, selected slices or planes, surface renderings, and the like.

In a preferred embodiment, each of the detector heads 20a–c receives both emission and transmission radiation and generates corresponding emission and transmission projection data.

The invention has been described with reference to the preferred embodiments. Obviously, modifications and alterations will occur to others upon a reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A nuclear medicine gamma camera for diagnostic imaging comprising:

a rotating gantry which defines a subject receiving aperture in which a subject is positioned;

a number of detector heads movably attached to the rotating gantry, said detector heads being rotated about the subject with rotation of the rotating gantry;

a number of radiation sources mounted to the detector heads such that penetrating transmission radiation from the radiation sources is directed toward and received by corresponding detector heads positioned across the subject receiving aperture from the radiation sources;

translation means which translate the detector heads laterally along paths tangential to the subject receiving aperture, said paths residing in a plane which is transverse to a longitudinal axis of the subject receiving aperture; and, a contouring device which determines outer boundaries of the subject in response to the transmission radiation received by the detector heads and controls the translation means accordingly.

2. The nuclear medicine gamma camera according to claim 1, wherein the rotating gantry is rotated such that the contouring device measures outer boundaries of the subject at a number of angular orientations to obtain a contour of the subject.

3. The nuclear medicine gamma camera according to claim 2, wherein the contour of the subject is obtained prior to running an imaging operation.

4. The nuclear medicine gamma camera according to claim 1, wherein:

the number of detector heads includes a first detector head and a second detector head arranged on the rotating gantry on opposite sides of the subject receiving aperture such that radiation receiving faces of the first and second detector heads face one another; and, the number of radiation sources includes;

a first radiation source mounted to the first detector head such that transmission radiation from the first radiation source is directed toward and received by the second detector head; and, a second radiation source mounted to the second detector head such that transmission radiation from the second radiation source is directed toward and received by the first detector head.

5. The nuclear medicine gamma camera according to claim 4, wherein the first and second radiation sources are mounted at opposite ends of the radiation receiving faces of the first and second detector heads, respectively.

6. The nuclear medicine gamma camera according to claim 5, wherein during a contouring operation the translation means translates the first and second detector heads laterally in opposite directions.

7. A nuclear medicine gamma camera comprising:

a rotating gantry which defines a receiving aperture in which a subject is positioned;

a first detector head, a second detector head, and a third detector head movably attached to the rotating gantry and arranged on the rotating gantry spaced from one another around the receiving aperture, said first, second and third detector heads being rotated about the subject with rotation of the rotating gantry;

translation means which translate the first, second and third detector heads laterally in directions tangential to the receiving aperture;

a first radiation source mounted to the first detector head such that radiation from the first radiation source is directed toward and received by the second detector head positioned across the receiving aperture from the first radiation source;

a second radiation source mounted to the second detector head such that radiation from the second radiation source is directed toward and received by the third detector head positioned across the receiving aperture from the second radiation source;

a third radiation source mounted to the third detector head such that radiation from the third radiation source is directed toward and received by the first detector head positioned across the receiving aperture from the third radiation source; and, a contouring device which determines outer boundaries of the subject in response to radiation received by the detector heads.

8. A nuclear medicine gamma camera comprising:

a rotating gantry which defines a receiving aperture in which a subject is positioned;

a number of detector heads movably attached to the rotating gantry, said detector heads being rotated about the subject with rotation of the rotating gantry;

a number of radiation sources mounted to the detector heads such that radiation from the radiation sources is directed toward and received by corresponding detector heads positioned across the subject receiving aperture from the radiation sources;

translation means which translate the detector heads laterally in directions tangential to the receiving aperture and move the detector heads in radial directions relative to the receiving aperture; and, a contouring device which determines outer boundaries of the subject in response to radiation received by the detector heads.

9. The nuclear medicine gamma camera according to claim 8, wherein the detector heads move such that an orbit traced by the detector heads as the rotating gantry rotates follows a contour of the subject defined by the outer boundaries determined via the contouring device.

10. A method of mapping outer boundaries of a subject being examined with a nuclear medicine gamma camera, the method comprising:

(a) placing the subject in a subject receiving aperture;

(b) positioning a number of radiation sources and corresponding radiation detectors about the subject receiving aperture such that the radiation sources are across the subject receiving aperture from their corresponding radiation detectors;

(c) directing penetrating radiation from the radiation sources toward their corresponding radiation detectors positioned across the subject receiving aperture;

(d) changing the relative positions of the radiation sources with respect to their corresponding radiation detectors; and, (e) measuring the outer boundaries of the subject in response to the radiation received by the radiation detectors.

11. The method according the claim 10, further comprising:

(f) incrementally rotating the radiation sources and corresponding radiation detectors about the subject receiving aperture such that measurements of the outer boundaries of the subject are taken at a number of angular orientations; and, (g) obtaining a contour of the subject from the measurements.

12. The method according to claim 11, wherein step (d) further comprises:

translating the radiation sources laterally in directions tangential to the subject receiving aperture.

13. A method of mapping an outer boundary of a subject, the method comprising:

(a) placing the subject in a receiving aperture;

(b) positioning a number of radiation sources and corresponding radiation detectors about the receiving aperture such that the radiation sources are across the receiving aperture from their corresponding radiation detectors;

(c) directing radiation from the radiation sources toward their corresponding radiation detectors positioned across the receiving aperture;

(d) translating at least one of the radiation sources and the radiation detectors laterally in directions tangential to the receiving aperture; and, (e) measuring the outer boundaries of the subject in response to radiation received by the radiation detectors.

14. A method of mapping an outer boundary of a subject, the method comprising:

(a) placing the subject in a receiving aperture;

(b) positioning a plurality of radiation sources and corresponding radiation detectors about the receiving aperture such that the radiation sources are across the receiving aperture from their corresponding radiation detectors;

(c) directing radiation from the radiation sources toward their corresponding radiation detectors positioned across the receiving aperture;

(d) translating two of the plurality of radiation sources laterally in directions opposite one another and tangential to the receiving aperture; and, (e) measuring the outer boundary of the subject in response to the radiation received by the radiation detectors.

15. The method according to claim 11, wherein:

step (b) further includes fixedly positioning each of the radiation sources on one of the radiation detectors; and, step (d) further includes translating the radiation detectors laterally in directions tangential to the subject receiving aperture.

16. A method of nuclear medical imaging, the method comprising:

(a) Placing a subject in a receiving aperture;

(b) positioning a number of radiation sources and corresponding radiation detectors about the receiving aperture such that the radiation sources are across the receiving aperture from their corresponding radiation detectors;

(c) directing penetrating radiation from the radiation sources toward their corresponding radiation detectors positioned across the receiving aperture;

(d) translating at least one of the radiation sources and the radiation detectors laterally in directions tangential to the receiving aperture;

(e) measuring an outer boundary of the subject in response to the radiation received by the radiation detectors;

(f) incrementally rotating the radiation sources and corresponding radiation detectors about the subject receiving aperture such that measurements of the outer boundary of the subject are taken at a number of angular orientations;

(g) obtaining a contour of the subject from the measurements; and, (h) selectively moving the radiation sources and corresponding radiation detectors relative to the subject in response to the obtained contour.

17. A method of nuclear medical imaging, the method comprising:

(a) placing a subject in a receiving aperture;

positioning a number of radiation sources and corresponding radiation detectors about the receiving aperture such that the radiation sources are across the receiving aperture from their corresponding radiation detectors;

(c) directing penetrating radiation from the radiation sources toward their corresponding radiation detectors positioned across the receiving aperture;

(d) translating at least one of the radiation sources and the radiation detectors laterally in directions tangential to the receiving aperture;

(e) measuring an outer boundary of the subject in response to the radiation received by the radiation detectors;

(f) incrementally rotating the radiation sources and corresponding radiation detectors about the subject receiving aperture such that measurements of the outer boundary of the subject are taken at a number of angular orientations;

(g) obtaining a contour of the subject from the measurements; and, (h) rotating the radiation sources and corresponding radiation detectors about the receiving aperture such that their orbit is determined in response to the obtained contour of the subject.

18. A method of diagnostic imaging including injecting a subject with a radiopharmaceutical, detecting radiation emitted from the radiopharmaceutical with a plurality of detector heads, and reconstructing an image from the detected radiation, the method further including:

translating the detector heads tangentially such that the emitted radiation is received off set from a center of the detector heads.

19. A method of diagnostic imaging including injecting a subject with a radiopharmaceutical, detecting radiation emitted from the radiopharmaceutical with three detector heads, and reconstructing an image from the detected radiation, the method further including:

translating the detector heads tangentially to a common circumferential direction and moving the detector heads radially inward such that an iris-like motion is achieved wherein the detector heads closely approach the subject without mechanically interfering with each other.

* * * * *